(12) United States Patent
Gremlich et al.

(10) Patent No.: US 8,686,116 B2
(45) Date of Patent: Apr. 1, 2014

(54) ACID SOLUBLE PROTEINS FROM MICELLAR CASEIN

(75) Inventors: Sandrine Gremlich, La Tour-de-Trême (CH); Lionel Bovetto, Larringes (FR); Catherine Mace, Lutry (CH)

(73) Assignee: Nestec S.A., Vevey (CH)

( * ) Notice: Subject to any disclaimer, the term of this patent is extended or adjusted under 35 U.S.C. 154(b) by 512 days.

(21) Appl. No.: 12/604,741

(22) Filed: Oct. 23, 2009

(65) Prior Publication Data
US 2010/0111933 A1    May 6, 2010

Related U.S. Application Data

(63) Continuation of application No. 10/570,184, filed as application No. PCT/EP03/09669 on Aug. 30, 2003, now Pat. No. 7,629,442.

(51) Int. Cl.
*A23J 1/20* (2006.01)
*C07K 1/00* (2006.01)

(52) U.S. Cl.
USPC .......................................... 530/360; 530/361

(58) Field of Classification Search
USPC ..................................... 514/12; 530/360, 361
See application file for complete search history.

(56) References Cited

FOREIGN PATENT DOCUMENTS

| | | |
|---|---|---|
| EP | 1367065 | 12/2003 |
| FR | 2673374 | 9/1992 |
| WO | WO 9831239 | 7/1998 |
| WO | WO 01/37850 | * 5/2001 |
| WO | WO 0137850 | 5/2001 |

OTHER PUBLICATIONS

Gesan-Guiziou et al., Process steps for the preparation of purified fractions of alpha-lactalbumin and beta-lactoglobulin from . . . , Journal of Dairy Research, 1999, 55:225-236.

Picon et al., The effect of liposome-encasulated cyprosins on Manchego cheese ripening, Journal of Dairy Research, 1996, 79:1699-1705.

Smithers et al., New casein products: Fresh opportunities for the dairy industry, vol. 51, No. 1/2, 1997: 92-98.

* cited by examiner

*Primary Examiner* — Tekchand Saidha
(74) *Attorney, Agent, or Firm* — K&L Gates LLP

(57) ABSTRACT

The present invention relates to a milk fraction obtainable by acidification of micellar casein and separation from precipitated casein named acid soluble protein from micellar casein. It was found that the milk fraction and especially certain sub-fractions thereof are bioactive and promote GLP-1 release in vitro. Based on these results, acid soluble protein from micellar casein may be useful in the treatment and the prevention of diabetes type II, obesity and may further be added to formulas directed at other purposes addressing the gastro-intestinal tract.

10 Claims, 3 Drawing Sheets

ACID SOLUBLE PROTEINS FROM MICELLAR CASEIN

This application is a continuation of application Ser. No. 10/570,184 filed on Jun. 5, 2006 now U.S. Pat. No. 7,629,442, which claims the benefit of PCT Application No. PCT/EP03/09669 filed on Aug. 30, 2003, which are hereby incorporated by reference in their entirety.

BACKGROUND

The present invention relates to a method of obtaining acid soluble proteins of micellar casein, to fractions of the proteins, to the proteins for use as a medicament and to the use of the proteins in the manufacture of medicament or consumable products.

Diabetes mellitus is one of the most widespread diseases in the world. There are two major forms of diabetes mellitus: type I and type II. Type I diabetic patients are characterised by an autoimmune destruction of their insulin secreting pancreatic beta cells. Type II diabetic patients, which represent 90-95% of all diabetic patients, are characterized by development of insulin resistance in the peripheral tissues (principally liver and muscle), and an inappropriate insulin secretion capacity.

People with type II diabetes are at high risk for serious long-term complications. These are essentially cardiovascular diseases, but also retinopathies, nephropathies and neuropathies.

Actual treatments for type II diabetes comprise several classes of drugs, which can be used alone or in combination with insulin, depending on the amount of insulin still produced (sulfonylureas, thiazolidinediones, for example). Eventually, when no insulin is produced any more, drug treatments may be replaced by injection of insulin alone.

Insulin biosynthesis and proinsulin gene expression are stimulated by Glucagon-Like Peptide-1 (GLP-1), expressed almost exclusively in endocrine intestinal cells. The important role of this secretagogue hormone is well summarised in "Glucagone-like peptide-1: a major regulator of pancreatic b-cell function, R. Perfetti and P. Merkel, European Journal of Endocrinology (2000), 143, 717-725, which document is incorporated herein by way of reference.

It was shown, for example, that after administration of intravenous GLP-1, the insulin secretory response type II diabetics was restored to that of normal patients.

Furthermore, GLP-1 inhibits gastric motility, gastric acid secretion, gastric emptying and delays enzymatic breakdown and absorption of nutrients. These affects are mostly preserved in both, type I and II diabetic patients Moreover, GLP-1 was demonstrated to have an effect on satiety and is likely to be involved in decreased food intake.

GLP-1 is thus considered to be an ideal candidate for the treatment of diabetes.

Moreover, whenever one molecule of GLP-1 is liberated, one molecule of Glucagon-Like Peptide-2 (GLP-2) is also liberated. Originating from one single mRNA, the mammalian proglucagon transcript. GLP-1 and GLP-2 are thus co-secreted in the gut.

GLP-2 inhibits gastric secretion and gastric motility. Chronic treatment with GLP-2 has beneficial trophic effects on the intestine, such as enhancing tissue mass and mucosal thickness, decreasing the rate of enterocyte apoptosis, just to mention a few. An overview on GLP-1 synthesis, secretion and biological activity may be derived from: Glucagon-Like Peptide 2, D. J. Drucker, The Journal of Clinical Endocrinology and Metabolism, 2001, 86, 1759-64.

In WO 01/37850 (Société des Produits Nestlé) for the first time an in vitro cell model to measure proglucagon gene expression and GLP-1 secretion is described. The cell-line is called NCI-H716 and is deposited, for example, under the ATCC number CCL-250. Accordingly, certain milk protein hydrolysates stimulate GLP-1 secretion.

WO 98/31239 describes a method for the selective hydrolysis of casein in the presence of at least one further protein constituent. It is mentioned that the preparations so obtained are beneficial with respect to diabetes.

The objective of the present invention is one or several molecules that stimulate the secretion of proglucagon derived hormones.

It is a further objective to find bio-active molecules that are considered nutritionally safe, for example, because they are naturally occurring in specific food resources.

Further objectives of the invention are to prevent or treat diabetes type II, to regulate glucose concentration in serum, to treat or prevent bowel disorders characterized by injury and/or dysfunction of the intestinal mucosal epithelium, to increase the thickness and surface area of the intestinal mucosa, and/or to decrease appetite and food intake.

It is also an objective of the present invention to improve GLP-1 and 2 delivery in humans and mammals.

SUMMARY

Surprisingly, a protein fraction of milk, which is usually associated with or in close interaction to micellar casein, is capable of stimulating the secretion of GLP-1. The very protein fraction may be liberated by exposing intact or enzyme treated casein to acidic conditions. Some of the proteins comprised in this fraction have never been characterised so far.

Consequently, in a first aspect the present invention provides a method of obtaining fractions of acid soluble proteins of micellar casein, comprising the steps of separating micellar or enzyme-treated casein and whey proteins, acidifying micellar casein or enzyme-treated casein to a pH below 6, separating acid soluble proteins from casein, and separating different fractions of acid soluble proteins.

In a second aspect the invention provides a sub-fraction of acid soluble proteins from micellar casein, characterised in that it is obtainable by hydrophobic interaction chromatography and that the fraction is eluted from a hydrophobic stationery phase by a mobile phase comprising 26.4 to 36 vol.-% acetonitrile.

In a third aspect the invention provides a sub-fraction of acid soluble proteins from micellar casein, characterised in that the fraction is obtainable by hydrophobic interaction chromatography and that it is eluted from a hydrophobic stationery phase by a mobile phase comprising 43.2 to 46.4 vol.-% acetonitrile.

In a fourth aspect, the present invention provides acid-soluble proteins from micellar casein for use as a medicament or preventive or therapeutic treatment of the human or animal body.

In a fifth aspect, the present invention provides the use of acid soluble proteins from micellar casein in the preparation of consumable products or medicaments to enhance insulin secretion and/or proinsulin gene expression.

In a sixth aspect, the present invention provides the use of acid soluble proteins from micellar casein in the preparation of consumable products or medicaments for the prevention or treatment of diabetes type I and/or II.

In a seventh aspect, the present invention provides the use of acid soluble proteins from micellar casein in the preparation of consumable products or medicaments to increase GLP-1 and/or GLP-2 secretion and/or to regulate glucose concentration in blood.

In a further aspect, the present invention provides the use of acid soluble proteins from micellar casein in the preparation of consumable products or medicaments for decreasing gastric emptying and acid secretion.

In yet a further aspect, the present invention provides the use of acid soluble proteins from micellar casein in the preparation of consumable products or medicaments for regulating appetite, decreasing food intake and/or increasing satiety.

In another aspect, the present invention provides a consumable product comprising any protein fraction or sub-fraction according to the present invention.

In another aspect, the present invention provides the use of acid soluble proteins from micellar casein in the preparation of consumable products or medicaments for treating intestinal disorders characterised by injury or dysfunction and/or to increase thickness and/or surface area of the intestinal mucosa.

An advantage of the present invention is that it provides naturally occurring active principles that are capable of stimulating secretion of GLP-1.

Another advantage of the present invention is that the protein fraction in question may be easily isolated and supplied in sufficient amounts to any food product.

A further advantage of the present invention is that it provides nutritionally safe principles that may be useful in the treatment or prevention of diabetes type I and/or II, Crohn's disease, short bowel syndrome, in the regulation of glucose levels in blood, and/or in the increase of a satiety feeling and decrease in food intake.

Additional features and advantages are described herein, and will be apparent from, the following Detailed Description and the figures

DETAILED DESCRIPTION

Figure 1:
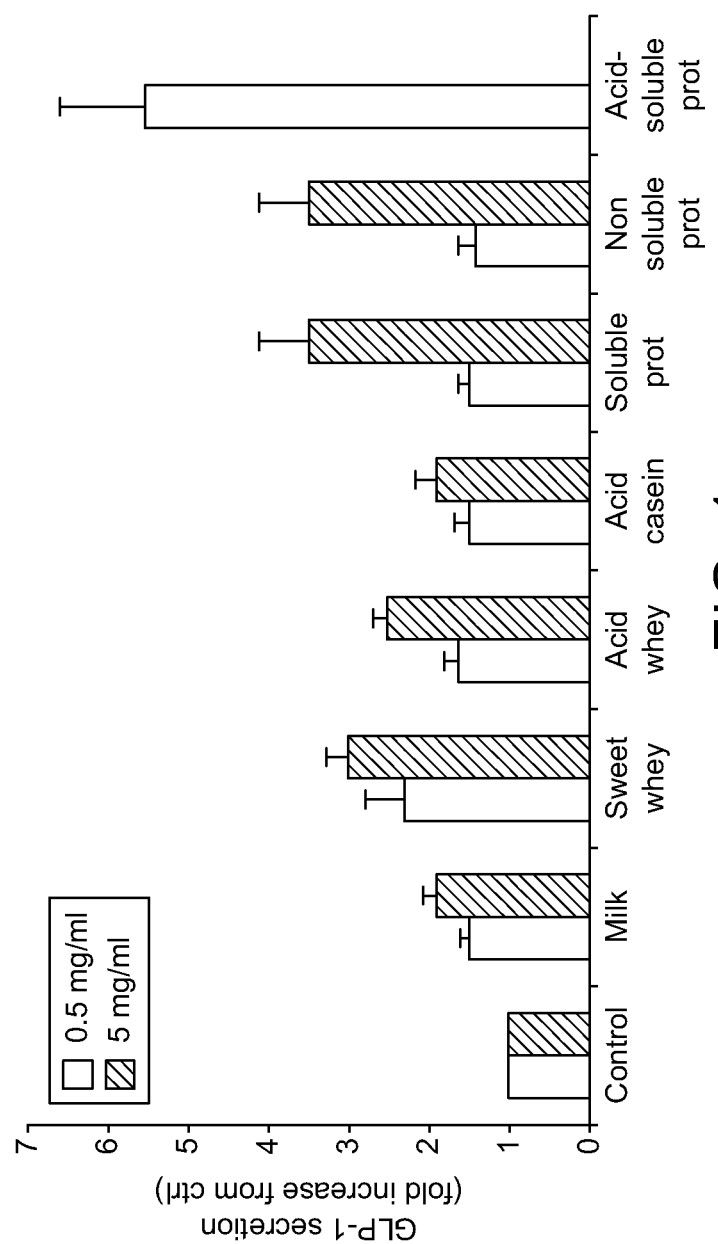
FIG. 1 compares the GLP-1 release in vitro stimulated by different protein fractions of bovine milk. The proteins were administered at 0.5 mg/ml (shaded bars) and 5 mg/ml (dark bars), with the exception of the acid soluble proteins of micellar casein according to the invention, which showed the highest effect on GLP-1 release even at low concentration (shaded bar). Milk extracts were prepared in Krebs-Ringer Balanced Buffer (KRBB), pH 7.4 comprising 0.2% BSA. The control consists of the buffer (KRBB) and BSA (0.2%) only FIG. 2 compares the GLP-1 release in vitro stimulated by different sub-fractions of acid soluble proteins of micellar casein. Different sub-fractions were administered in identical concentrations (30 µg/ml), and it is found that especially the sub-fractions 5, 7, 8, 10, and 11 show a prominent effect on GLP-1 secretion. The total, which comprises the original mixture of all 14 fractions, was administered at much higher concentration (5 µg/ml).

Within the context of this specification the word "comprises" is taken to mean "includes, among other things". It is not intended to be construed as "consists only of".

In the context of the present invention, the term consumable product is intended to encompass any nutritionally complete or supplementary consumable product. Hence, the composition may be consumed by humans, pets, such as cats and dogs, for example, and/or other animals. It may, be a bar, a snack, a nutritional formula, such as a liquid or powdered and reconstitutable formula, an infant or baby formula, an ice cream, a dairy product, a confectionery product, or it may be a supplement or a medicament, which may, optionally, be added to another food product, such as the ones given above. It may also be a liquid product.

For example, if the food product is a nutritional formula, it may be an exclusive formula or a supplemental formula. An exclusive formula is usually consumed in an amount of 1.8 to 2.2 L daily by adults, and from 0.6 to 1.4 L daily by infants.

If the formula is used supplementary, the daily amount is about ⅛ to about 1/12 of the amounts for exclusive formulas, for example.

However, a consumable product according to the present invention is not restricted to any product. It may be a food product itself or an ingredient or component of any food product.

With respect to the method of acid soluble proteins of micellar casein, the separation of native or micellar casein from whey proteins, or of enzyme treated casein from whey proteins, may be performed in many ways, such as by ultracentrifugation, or microfiltration, for example. Whey proteins may also be separated from casein by selective removal of specific whey proteins, for example according to their hydrophobic properties.

Acidification of micellar or enzyme treated casein is made by adjusting pH below 6, preferably below 5, more preferably below 4.8, for example, 4.6. Any acid may be suitable, as long as it is food grade, such as HCl, acetic acid, and so forth.

Separation of acid soluble casein from micellar casein may again be done by any suitable method, such as ultracentrifugation, filtration, decantation, and other.

Separation of different sub-fractions of acid soluble proteins may be done according to hydrophobic properties, for example by hydrophobic interaction chromatography (HIC), hydrophobic interaction liquid chromatography (HI-HPLC) and methods based on similar principles. Also other methods may be suitable, such as separation exploiting size or charge properties of different fractions, for example.

With respect of the sub-fractions of acid-soluble proteins according to the invention, they may be defined by their elution characteristics as given in Table 1. Table 1 shows that the fraction eluted in the range of an acetonitrile concentration of 26.4 to 36 vol-%, corresponds to a range of 33 to 45 vol.-% of buffer B in a mixture consisting of Buffer A and B as defined below Table 1.

The ranges of Buffer B and Buffer A concentrations above are sufficient to characterise the eluted protein fraction (Table 1). For the above elution ranges, preferably polystyrene-divinylbenzene beads are used as a stationary phase. Preferably, the product under the catalogue No. 15 RPC TN 17-0727-02 from Amersham is used as a stationery phase.

In particular, the pH of elution according to the above characteristics may generally be in the range of 1.8 to 2.2, preferably about 2. This pH is mainly defined by the amount of trifluoroacetic acid TFA).

In addition to presumably unknown substances, it is likely that sub-fraction 6, 7 and 8 comprise PP8 (proteose peptone), fractions 8 and 9 comprise PP8 and PP5 (proteose peptones), fraction 10 comprises lactoferrin and fraction 11 comprises β-lactoglobulin.

Thus, in preferred embodiments according to the invention, the sub-fractions according to the present invention are sub-fractions 5, 6, 7, 8, 10, and 11 as characterised in Table 1 by elution at specific buffer or acetonitril concentration ranges. Sub-fraction 5, specifically, may be re-tested additionally, because some cytotoxic properties are suspected.

A possible way of working the present invention is by first isolating the specific milk protein fractions reported herein. This may be done in any adequate way and there are at least a few procedures suitable.

For example, acid-soluble proteins from micellar casein may be obtained by isolating casein from milk or skimmed milk (or derivatives) by ultracentrifugation. Accordingly, skimmed milk is ultra-centrifuged at 30'000 to 90'000 g or up to 110'000 g for 45 to 90 min, for example. The sediments may be recovered, constituting micellar casein (or: non-soluble proteins).

The micellar casein may be washed by dispersing it in $CaCl_2$ 2 mM/NaCl 0.9% and ultra-centrifuged as above.

Acid-soluble proteins from casein may then be obtained by acidification of the washed micellar casein, as described above. For example, micellar casein (non-soluble protein) may be dispersed in sodium acetate buffer 20 mM pH 4.6. Due to casein buffering behaviour, a pH of about 4.6 may be achieved by acetic acid (or other suitable acid) addition.

The solution may then be centrifuged (9'000 to 15'000 g, 20 to 50 min, for example) and the supernatant may be collected as acid-soluble protein from micellar casein.

Another way of obtaining acid-soluble proteins from micellar casein may be derived from: Protein composition of micellar casein obtained by cross-flow micro-filtration of skimmed milk, R. Jost, R. Brandsma, S. Rizvi, International Dairy Journal 9 (1999) 389-90.

Accordingly, native casein is obtained by micro-filtration instead of ultra-centrifugation. Hence, micro-filtration membranes with pore sizes in the range of 0.1-0.2 μm are used to separate the micellar phase of milk from its serum phase by a purely physical process.

For example, skimmed milk warmed to 50° C. may be filtered through a 1P19-40 Tetra-Laval 1.4 μm Membralox® module to reduce its bacterial load. Then it may be warmed to 55° C. and separated on a Tech-Sep 1S 151 micro-filtration unit equipped with Carbosep® M14 (0.14 μm pore size) membranes. The milk may thus be fractionated into a retentate and a permeate stream, operating in a concentration mode. After reaching concentration factor 3 (cf3), diafiltration may be initiated by addition of demineralized water. The retentate obtained after diafiltration of 6 initial volumes of water (cf3/df6) constitutes micellar casein.

The acid-soluble parts of micellar casein may then be obtained by acidification of rediluted retentate with hydrochloric (or other, such as acetic) acid to pH 4.6, followed by separation of curd by centrifugation. As a result, 3-5% of the total N may be separated from the curd as acid-soluble proteins of micellar casein.

In so doing a protein fraction comprising, amongst other, lactoferrin, serum albumin, immunoglobulin H- and L-chains, and a protein having an electrophoretic mobility similar to β-lactoglobulin may be obtained.

Furthermore, the fraction may comprise proteose peptone component 5 (β-casein 1-105/1-107) and proteose peptone component 8 fast.

Other components of the acid-soluble proteins of micellar casein are defined by the present invention.

Of course, the above methods just serve as examples for the isolation or purification of acid-soluble proteins from micellar casein. The skilled person may easily envisage other methods for obtaining them.

For example, it is possible that acid-soluble proteins of micellar casein remain attached at least partially to casein after enzyme treatment (for example, rennet). In this case, acid-soluble protein of micellar casein may be obtainable by treating milk enzymatically, followed by recovering the curd formed by the coagulated casein. The acid-soluble fraction of micellar casein may then be at least partially isolated from the curd by acidification as above, for example.

Such a procedure would replace the isolation of micellar casein by centrifugation or ultrafiltration, in so far as the acid-soluble proteins of micellar casein mainly remain associated to the cleaved casein fractions.

It may also be possible to recover the acid-soluble proteins of micellar casein by acidifying milk or skimmed milk. Then the proteins according to the present invention must be separated from the acid whey, the latter further comprising other soluble milk components comprised in acid whey (mainly α-lactablumin, β-lactoglobulin, lactoferrin). This may be done by any suitable separation technique suitable to remove selectively the whey fraction mentioned above, for example by HIC or ion exchange chromatography.

The present invention is based on the surprising cognition that acid soluble proteins of micellar casein comprise bioactive principles that are suitable to promote GLP-1 and (therewith connected) GLP-2 release.

However, further sub-fractionation of the acid soluble proteins from micellar casein and screening reveals that some sub-fractions of the acid soluble proteins of micellar casein are preferred.

Further separation and isolation of more effective sub-fractions may be achieved by hydrophobic interaction chromatography (HIC), or by hydrophobic interaction high performance liquid chromatography (HI-HPLC), reversed-phase high-performance liquid chromatography (RP-HPLC), and the like, all of which are based on the same separation principles, for example.

The principles of HIC are known to the skilled person. Generally, samples are loaded onto an equilibrated column (stationery phase) comprising a hydrophobic material retaining the samples. The hydrophobic material may be, for example, macroporous crosslinked polystyrene, commercialised as Amberlite Xad 16 (XAD 16 from Rohm and Hass), for example. 15 RPC TN 17-0727-02 (polystyrene-divinylbenzene) from Amersham or equivalents may also be used.

Before the protein fraction according to the invention is loaded onto the column, the latter may be equilibrated with a buffer. After the fraction is loaded, a buffer or a mixture of buffers (mobile phase) may be run over the column, whereby the mixture of buffers varies and may have, therefore, varying properties of eluting protein sub-fractions according to their hydrophobicity from the column.

Separation of whey proteins according to this method is described in: "Simultaneous separation and quantitation of the major bovine whey proteins including proteose peptone and caseinomacropeptide by reversed-phase high-performance liquid chromatography on polystyrene-divinylbenzene", D. F. Elgar et al., Journal of Chromatography A 878 (2000) 183-196.

The protein sub-fractions eluted from the column may accurately be described by the composition of the buffer mixture or acetonitrile content that effected their elution from the stationery phase.

For example, acid soluble proteins from micellar casein may be loaded onto a column filled with polystyrene-divinyl-benzene beads (15 RPC TN 17-0727-02 from Amersham), a buffer A may be defined as 0.1 vol.-% trifluoroacetic acid (TFA) in water and a buffer B may be defined as 80 vol-% acetonitril and 0.85 vol.-% TFA in water.

Then, the mixing and transport of buffers A and B may be controlled by a specific system, for example a FPLC (Fast Protein Liquid Chromatography) UNICORN station (Pharmacia, Amersham), and flown through the column.

The eluted protein sub-fraction may be defined by an elution range of mixing-ratios of the above mentioned buffers A and B. Using the specific buffer composition, the elution moment or interval of a protein sub-fraction may be described simply by the relative amount of acetonitrile present at the moment of elution of a protein fraction according to the invention. It should be noted, however, that the elution order is pH dependent.

Table 1 below defines 14 acid soluble protein sub-fractions of the acid-soluble protein from micellar casein according to the invention by a vol.-percentage range of buffer B, or a range in acetonitrile, within which sub-fractions according to preferred embodiments of the present invention are eluted.

TABLE 1

Sub-fractions of acid soluble proteins from micellar casein defined by hydrophobic interaction chromatography.

| fraction | % B Buffer start | % B Buffer end | % acetonitrile start | % acetonitrile end |
|---|---|---|---|---|
| 1 | 20 | 22.5 | 16 | 18 |
| 2 | 22.5 | 26 | 18 | 20.8 |
| 3 | 26 | 30 | 20.8 | 24 |
| 4 | 30 | 33 | 24 | 26.4 |
| 5 | 33 | 36 | 26.4 | 28.8 |
| 6 | 36 | 39.5 | 28.8 | 31.6 |
| 7 | 39.5 | 43.5 | 31.6 | 34.8 |
| 8 | 43.5 | 45 | 34.8 | 36 |
| 9 | 45 | 49 | 36 | 39.2 |
| 10 | 49 | 54 | 39.2 | 43.2 |
| 11 | 54 | 58 | 43.2 | 46.4 |
| 12 | 58 | 67.5 | 46.4 | 54 |
| 13 | 67.5 | 81.5 | 54 | 65.2 |
| 14 | 81.5 | 100 | 65.2 | 80 |

Buffer A: Water TFA 0.1%
Buffer B: Acetonitrile/Water/TFA (80%/19.15%/0.85%; v/v)
Column: Source 15 RFC Amersham (matrix: Polystyrene/divinyl benzene), column volume (CV = 100 ml)
Gradient: starting from 20% B Buffer, sample was injected after 1 column volume (CV), then gradient increased up to 75% B in 15 CV then 2 CV to reach 100% B Buffer If desirable, the sub-fractions may be concentrated by evaporation, ultrafiltration, or dialysed to eliminate organic solvent before drying, for example by vacuum-, freeze-, spray-, fluidised bed-, oven-, or any other suitable drying process.

Sub-fractions 5, 6, 7, 8, 9, 10, and 11 are specifically effective in promoting GLP-1 release in vitro and constitute a preferred embodiment in the sense of the present invention. Sub-fractions 5, 7, 8 and 11 constitute an even more preferred embodiment.

Sub-fraction 5 has been shown to have a toxic effect on cells of an in vitro model, hence this fraction may prove to have diminished applicability in humans or animals.

Acid soluble proteins of micellar casein comprise biologically active principles that enhance GLP-1 secretion in an in vitro model.

Therefore, the fraction or selected sub-fractions may be used for regulation of any process dependent or controlled by GLP-1, GLP-2 or insulin. Examples are the prevention or treatment of diabetes I or II, regulation of blood glucose concentration, inhibition of gastric motility and secretion, decrease gastric emptying rate of liquids and solids, decrease small intestine transit, inhibition of smooth muscle activity, decrease meal-induced glucose excursions, delay of enzymatic breakdown and absorption of nutrients in the intestines, decrease of appetite, decrease of food intake, and the like.

For example, the fraction may be used to decrease overall digestive and absorptive activity of a human or an animal.

The protein fraction may be added to consumable products or medicaments. Examples of consumable products are nutritional formulas, infant formulas or clinical formulas. Other examples are drinks, for example shelf stable, chilled or ready-to-drink beverages. The fractions may be added to other food products, such as chocolate, bars, cereals, dairy products, ice cream, frozen food, pet food, coffee, capsule, tablet, for example.

The following examples are given by way of illustration only and in no way should be construed as limiting the subject matter of the present application. Percentages and parts are by weight unless otherwise indicated.

EXAMPLE 1

Isolation of Acid Soluble Protein from Micellar Casein

Bovine milk was obtained from a local market (Switzerland, Toni lait, 2000-02-01).

Cream was extracted from whole milk by centrifugation between 1'000 and 4'500 g. The selectivity of this step was improved by increasing acceleration up to 13'600 g using fixed-angle rotor Sorvall GS3 (9'000 rpm during 30 minutes). Starting from 2'200 ml of whole milk, 90 g of cream were recovered in the top layer.

Then, 250 µl of $CaCl_2$ 200 mM were added to 250 ml of skimmed milk to reach a final 2 mM concentration. This milk was ultra-centrifuged (6 tubes containing 42.1 g of skimmed milk) 1 hour in a fixed-angle rotor 45 TI (Beckman L8-60M ultracentrifuge; 32'000 rpm corresponding to 100'000 g in the middle of the tube) to separate whey from non-soluble micellar casein.

Micellar casein (24 g) was dispersed in 220 ml $CaCl_2$ 2 mM/NaCl 0.9% and ultra-centrifuged as above. The 22 g washed micellar casein recovered were dispersed in $CaCl_2$ 2 mM/NaCl 0.9% and volume adjusted to 250 ml. It was aliquoted, labeled non-soluble proteins (micellar casein) and frozen.

Starting from 190 g whole milk the deposit of washed non-soluble proteins (17 g) was dispersed (Potter) in 40 ml sodium acetate buffer 20 mM pH 4.6.

Due to casein buffering behavior, pH (6.5) was adjusted to 4.6 by acetic acid addition, and volume was adjusted to half initial milk volume (90 ml) by acetate buffer addition. Solution was then centrifuged (12'000 g, 30 min) and supernatant (77 g) was labeled Acid-soluble protein from micellar casein.

For the purpose of Example 3 below, the sample was frozen by immersion in liquid nitrogen and stocked at −20° C.

EXAMPLE 2

GLP-1 Release Promoted by Different Milk Fractions

Material and Methods

MH (meat hydrolysate) and EAH (egg albumin hydrolysate) were purchased from Sigma. Matrigel was from BD Bioscience. CGMP was obtained as described in WO 9853702.

Fractionation steps to obtain skimmed milk, sweet whey, acid whey, acid casein, soluble proteins, non-soluble proteins (micellar casein) were adapted from conventional milk processes (see: Alais C. 1984 Science du lait, Principe des Techniques Laitières, 4ème édition, SEPAIC, Paris, 29-35, 159-178). Centrifugation was performed at higher acceleration rates and non-soluble fractions were washed to increase selectivity and separation efficacy.

Acid casein is casein collected from sediments after acid treatment of skimmed milk.

Soluble proteins are proteins recovered in aqueous solution after ultracentrifugation of skimmed milk for 1 h at 100'000 g (see also Example 1), non-soluble protein (micellar casein) being the part recovered in sediments thereafter.

Acid-soluble proteins from micellar casein were taken from Example 1, basically obtained by acidifying and centrifuging the resulting acid casein of the above paragraph.

NCI-H716 human intestinal cell line (ATCC number: CCL-251) was cultured at 37° C. in a humidified incubator containing 5% $CO_2$. For proliferation, cells were grown in suspension in RPMI 1640 medium (Life Technologies Inc) supplemented with 10% FBS, 100 IU/ml penicillin, 100 μg/ml streptomycin and 2 mM L-glutamine. For secretion studies, cells were plated on Matrigel-coated plates, and incubated 2 days in DMEM (low glucose) (Life Technologies Inc) supplemented with 10% FBS, 100 IU/ml penicillin, 100 μg/ml streptomycin and 2 mM L-glutamine.

Two days before the experiment, cells were plated at 1 million cells/well in 12-wells plates. On the day of the experiment, cells were washed once with HBSS (Hank's Balanced Salt Solution; Life Technologies Inc), and incubated during two hours at 37° C. in the presence of the different protein solutions. Test proteins were dissolved in 1 ml of KRBB (Krebs-Ringer Balanced Buffer) pH 7.4 containing 0.2% BSA (fraction V; Sigma). At the end of the incubation period, supernatant was recovered in 10 μl PMSF 200 mM and immediately frozen at −80° C.

Protein solutions were added in two concentrations, 0.5 and 5 mg protein per ml medium.

Results

FIG. 1 shows the effect of different milk protein fractions at different concentrations (0.5 and 5 mg/ml) on GLP-1 release in vitro. Acid-soluble proteins from micellar casein obtained according to Example 1 have the highest impact on GLP-1 release even at low concentration (0.5 mg/ml).

In conclusion, acid-soluble proteins from micellar casein, obtainable by the method according to Example 1 comprise bio-active principles. These may be used in the prevention of disease or therapy of the human or animal body. The release of GLP-1 suggests usefulness and industrial applicability of these principles in the prevention and treatment of diabetes and obesity, for example.

EXAMPLE 3

Sub-Fractionation of Acid Soluble Protein from Micellar Casein

A hydrophobic interaction liquid chromatography (HIC) was performed as follows. A HR16x50 column filled with 100 ml Source 15 RPC TN 17-0727-02 (polystyrene-divinylbenzene) was connected to a FPLC system controlled by a UNICORN station (Amersham Pharmacia Biotech). 15 ml of HCl acid-soluble fraction (see Example 1) were thawed 20 min in a water-bath at 37° C., mixed by vortexing and centrifuged 1 min at 13'000 rpm in a 5415 Eppendorf centrifuge. After filtering on a 0.45 μm Millipore filter (306/GSWP04700.GS), 10 ml of this preparation was injected.

Chromatographic conditions were: A buffer: TFA 0.1% in water (2'000 ml of miliQ water filtered on a 0.45 μm Millipore system, plus 2 ml TFA (Sigma 91699, 100 ml)); B buffer: acetonitrile 80%, TFA 0.85% (400 ml of miliQ water filtered on a 0.45 μm Millipore system, plus 1'600 ml acetonitrile, degassed in an ultrasound bath during 15 minutes, and finally additionned with 1.7 ml TFA).

Column was equilibrated with 20% B buffer. Then, after one column volume (CV), sample was injected, B buffer increased to 75% in 15 CV and to 100% in 2.5 CV. At the end, gradient decreased to 20% B buffer in 0.4 CV. Flow rate was fixed at 3 ml/min.

96 fractions of 18 ml were collected in plastic tubes. Fractions were kept at −20° C. After HPLC analysis, the 96 collected tubes were pooled in 14 fractions by similitude of HPLC profile and concentrated by evaporation before lyophilisation for subsequent screening.

Figure 3:
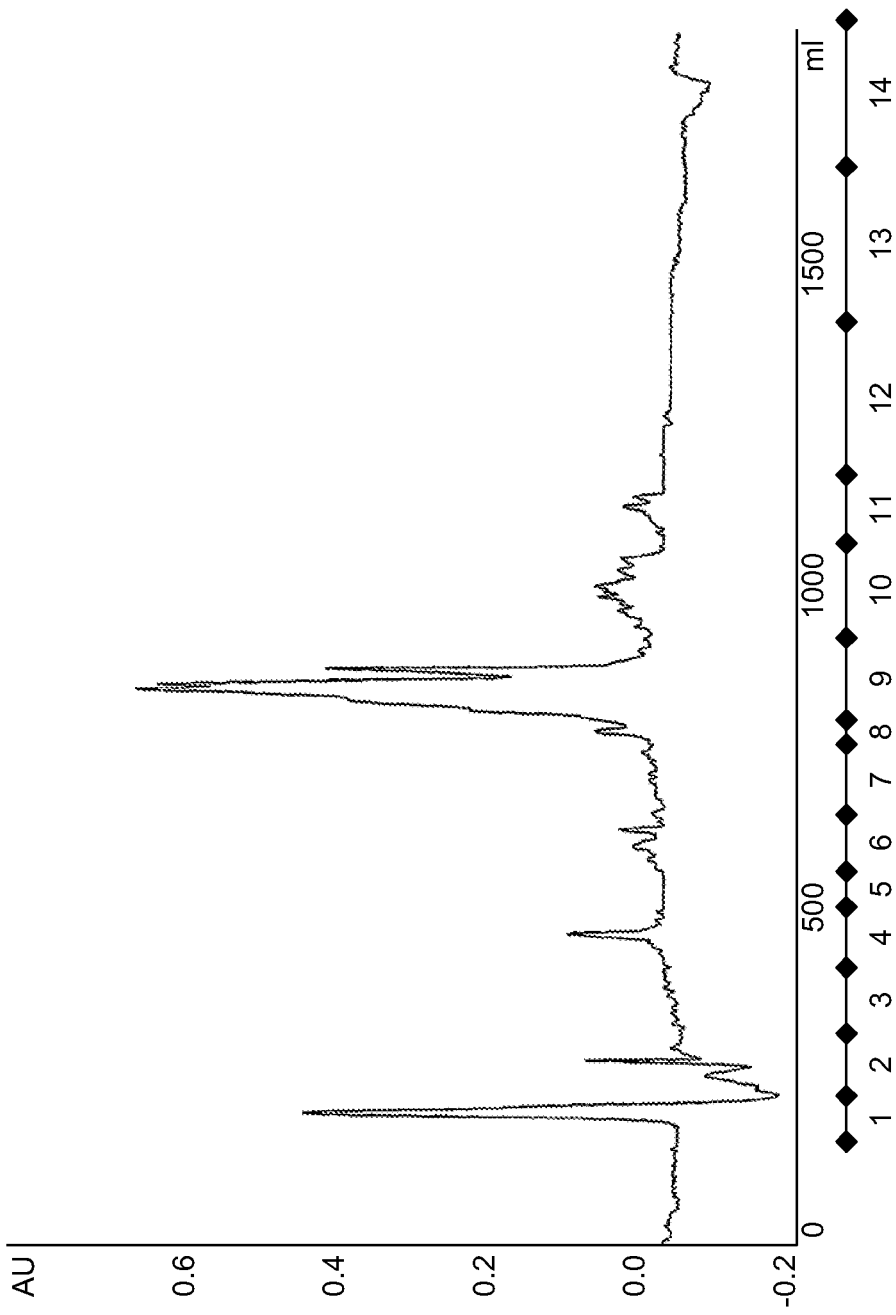
FIG. 3 shows a HI-HPLC (hydrophobic interaction-high performance liquid chromatography) chromatogram of 14 fractions of acid soluble proteins from micellar casein. The horizontal axis illustrates increasing hydrophobicity of acid soluble proteins from micellar casein, which were partitioned into said 14 different sub-fractions. The vertical axis indicates the amount of protein eluted from the column, measured by UV at 214 nm.

UV absorption at 215 nm was recorded, the corresponding HIC profile is given in FIG. 3

The 14 sub-fractions of acid-soluble proteins from micellar casein are characterised by way of their moment of elution from the column and the corresponding Acetonitrile concentration (hydrophobicity) in Table 1 of the description.

EXAMPLE 4

GLP-1 Release Promoted by Sub-Fractions of Example 3

The sub-fractions obtained in Example 3 were screened for GLP-1 release promoting capacity according to the experimental design as set out in Example 2. All sub-fractions were tested at 30 μg/ml media, except for "total", comprising all sub-fractions, which was tested at 500 μg/ml.

It is mentioned that in this experiment, hydrophobic chromatography pools were tested at a concentration 16-17 times lower than the initial acid-soluble proteins from micellar casein of Example 2 (30 μg/ml compared to 500 μg/ml).

Figure 2:
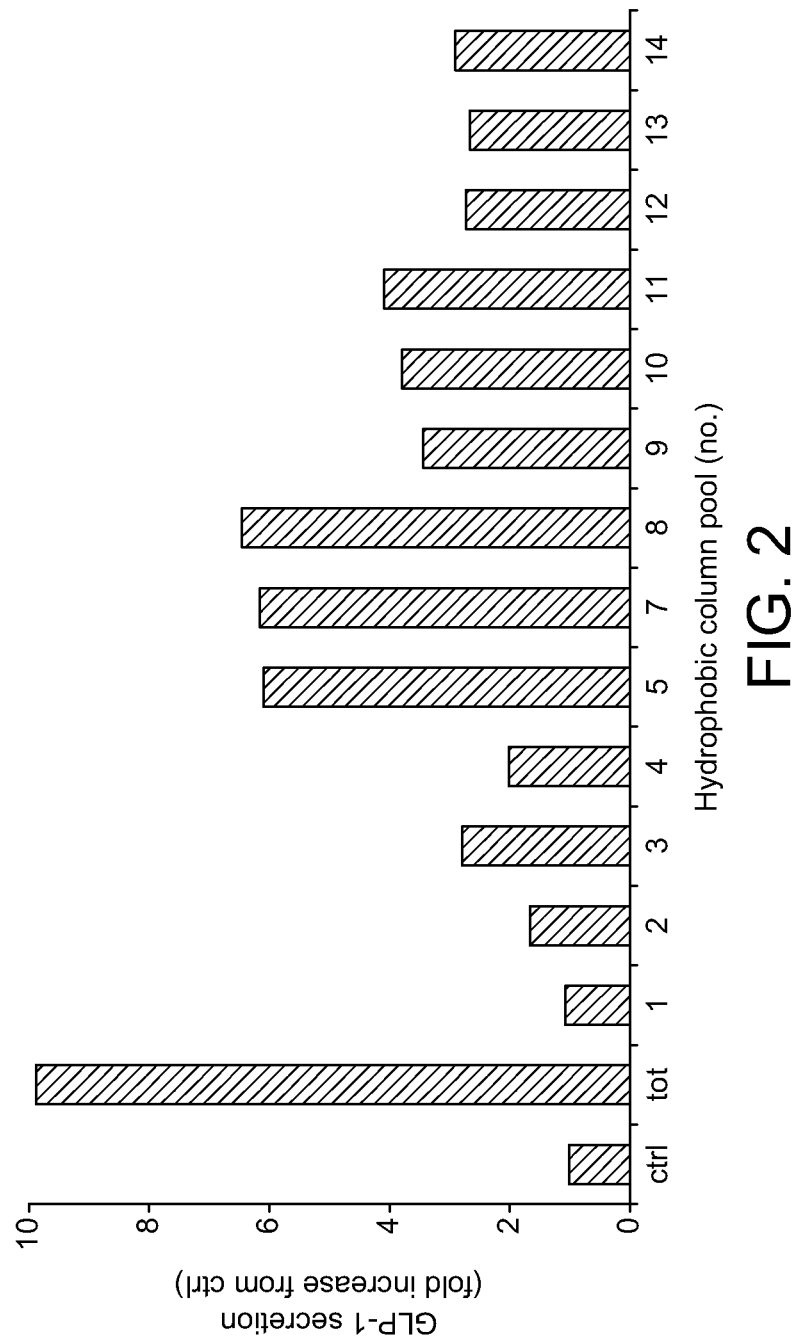

The result is shown in FIG. 2. Nearly all fractions caused an increase of GLP-1 release in vitro. Extraordinarily strong increase is found with sub-fractions 5, 7, 8, but also with 9, 10, and 11 at very low protein concentrations (30 μg protein/ml media).

It was found, however, that sub-fraction 5 has toxic effect on the cell-line.

In conclusion, sub-fractions 7, 8, 9, 10, and 11 comprise bio-active molecules or principles. These may serve as medicaments, especially in the treatment of diabetes type II, possibly also type I or obesity. The various other effects of GLP-1 in the human or animal body explain further applications of the sub-fractions as given in the claims.

EXAMPLE 5

A Nutritional Formula Comprising Acid-Soluble Proteins from Micellar Casein

A nutritional formula comprising, in percent by weight of dry matter, 14% protein, 62% carbohydrate, 18% fat and 3.2% minerals and vitamins according to recommended values (315 kJ/dl), is completed with acid soluble protein from micellar casein according to Example 1.

The acid soluble protein is added in physiologically effective amounts. In a complete, exclusive formula (Intended consumption is 2 1 per day) the final concentration was adjusted to 0.1-0.5 mg/ml of the formula. In formula useful as a supplement to other nutrition (intended consumption: 2 dl per day) the concentration was adjusted to 1-5 mg/ml formula. Higher doses are used according to circumstance and individual requirements.

EXAMPLE 6

A Nutritional Formula Comprising Sub-Fractions Acid-Soluble Proteins from Micellar Casein The formula of Example 5 is enriched with protein of sub-fractions 7 and 8 obtained in Example 3 instead of protein according to Example 1.

The amount of dry matter of the sub-fractions in the nutritional formula is adjusted to be 5-25 µg/ml liquid formula for a complete formula (see Example 5), and 50-250 µg/ml for a daily dose of 2 dl (supplement).

A high dose formula comprising the sub-fractions was also prepared, (10 times concentrated with respect to the 2 dl supplement above). The concentration of the proteins according to the invention was 0.5-2.5 mg/ml in 2 dl.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention claimed is:

1. A method for enhancing insulin secretion and/or proinsulin gene expression comprising the steps of administering to an individual a composition comprising an acid soluble protein fraction obtained from micellar casein by a process comprising separation of the micellar casein from whey, acidification of the micellar casein to a pH below 6, separation of acid soluble proteins from the acidified micellar casein, and separation of different fractions of the acid soluble proteins based on the hydrophobic properties of the fractions.

2. A method for treating diabetes comprising the steps of administering to an individual having diabetes a composition comprising an acid soluble protein fraction obtained from micellar casein by a process comprising separation of the micellar casein from whey, acidification of the micellar casein to a pH below 6, separation of acid soluble proteins from the acidified micellar casein, and separation of different fractions of the acid soluble proteins based on the hydrophobic properties of the fractions.

3. The method of claim 2 wherein the diabetes is type I.

4. The method of claim 2 wherein the diabetes is type II.

5. The method of claim 1 wherein the acid soluble protein fraction obtained from micellar casein is a sub-fraction of acid soluble proteins obtained from micellar casein by hydrophobic interaction chromatography, the fraction being eluted from a hydrophobic stationery phase by a mobile phase comprising 26.4 to 36 vol.-% acetonitrile.

6. The method of claim 1 wherein the acid soluble protein fraction obtained from micellar casein is a sub-fraction of acid soluble proteins obtained from micellar casein by hydrophobic interaction chromatography, the fraction being eluted from a hydrophobic stationery phase by a mobile phase comprising 43.2 to 46.4 vol.-% acetonitrile.

7. The method of claim 1 wherein the acid soluble protein fraction obtained from micellar casein is a sub-fraction of acid soluble proteins obtained from micellar casein by hydrophobic interaction chromatography, the fraction being eluted from a hydrophobic stationery phase by a mobile phase comprising 31.6 to 36 vol.-% acetonitrile.

8. The method of claim 2 wherein the acid soluble protein fraction obtained from micellar casein is a sub-fraction of acid soluble proteins obtained from micellar casein by hydrophobic interaction chromatography, the fraction being eluted from a hydrophobic stationery phase by a mobile phase comprising 26.4 to 36 vol.-% acetonitrile.

9. The method of claim 2 wherein the acid soluble protein fraction obtained from micellar casein is a sub-fraction of acid soluble proteins obtained from micellar casein by hydrophobic interaction chromatography, the fraction being eluted from a hydrophobic stationery phase by a mobile phase comprising 43.2 to 46.4 vol.-% acetonitrile.

10. The method of claim 2 wherein the acid soluble protein fraction obtained from micellar casein is a sub-fraction of acid soluble proteins obtained from micellar casein by hydrophobic interaction chromatography, the fraction being eluted from a hydrophobic stationery phase by a mobile phase comprising 31.6 to 36 vol.-% acetonitrile.

* * * * *